United States Patent
Lindblad-Toh et al.

(10) Patent No.: US 6,440,675 B1
(45) Date of Patent: Aug. 27, 2002

(54) METHODS FOR SELECTING PRIMERS

(75) Inventors: Kerstin A. Lindblad-Toh, Malden; Ellen Winchester, Cambridge; Joel N. Hirschhorn, Newton; Pamela Sklar, Brookline, all of MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/663,902

(22) Filed: Sep. 18, 2000

Related U.S. Application Data

(60) Provisional application No. 60/154,550, filed on Sep. 17, 1999.

(51) Int. Cl.⁷ .............................. C12Q 1/68; C12P 19/34
(52) U.S. Cl. ........................................... 435/6; 435/91.2
(58) Field of Search ..................... 435/6, 91.2

(56) References Cited

U.S. PATENT DOCUMENTS 5,391,740 A    2/1995   Wang et al. ................. 544/319

OTHER PUBLICATIONS

Freier, S.M. et al., "Improved free–energy parameters for predictions of RNA duplex stability", PNAS vol. 83, pp. 9373–9377 (1986).*

Jolley, M.E., et al., "Fluorescence Polarization Immunoassay. III. An Automated System for Therapeutic Drug Determination," *Clin. Chem.*, 27(9) :1575–1579 (1981).

Popelka, S.R., et al., "Fluorescence Polarization Immunoassay II. Analyzer for Rapid, Precise Measurement of Fluorescence Polarization with Use of Disposable Cuvettes," *Clin. Chem.*, 27(7) :1198–1201 (1981).

Dandliker, W.B., et al., "Fluorescence Polarization Immunoassay. Theory and Experimental Method," *Immunochemistry*, 10:219–227 (1973).

Dandliker, W.B., and de Saussure, V.A., "Fluorescence Polarization in Immunochemistry," *Immunochemistry*, 7:799–828 (1970).

Jolley, M.E., "Fluorescence Polarization Immunoassay for the Determination of Therapeutic Drug Levels in Human Plasma," *J. of Analytical Toxicology*, 5:236–240 (1981).

Chen, X., et al., "Fluorescence Energy Transfer Detection as a Homogeneous DNA Diagnostic Method," *Proc. Natl. Acad. Sci USA*, 94:10756–10761 (1997).

Chen, X., et al., "Fluorescence Polarization in Homogeneous Nucleic Acid Analysis," *Genome Research*, 9:492–498 (1999).

Rychlik, W., "Selection of Primers for Polymerase Chain Reaction," *Molecular Biotechnology*, 3(2) :129–134 (1995).

Lowe, T., et al., "A Computer Program for Selection of Oligonucleotide Primers for Polymerase Chain Reactions," *Nucleic Acids Research*, 18 (7) :1757–1761 (1990).

Rychlik, W., and Rhoads, R.E., "A Computer Program for Choosing Optimal Oligonucleotides for Filter Hybridization, Sequencing and In Vitro Amplification of DNA," *Nucleic Acids Research*, 17 (21) :8543–8551 (1989).

* cited by examiner

*Primary Examiner*—Kenneth R. Horlick
*Assistant Examiner*—Teresa Strzelecka
(74) *Attorney, Agent, or Firm*—Hamilton, Brook, Smith & Reynolds, P.C.

(57) ABSTRACT

Methods for selecting primers having a reduced incidence of undesirable interactions are disclosed. Methods of improving the accuracy of SBE-fluorescence polarization (SBE-FP) methods are also disclosed.

2 Claims, 1 Drawing Sheet

"Foldback" in SBE primers

TAAAACGTCGCCGCCTTCGATTGATGGCGATCG

↓

—————————————TCGAT
                GCTA

↓

TAAAACGTCGCCGCCTTCGATTGATGGCGATCG

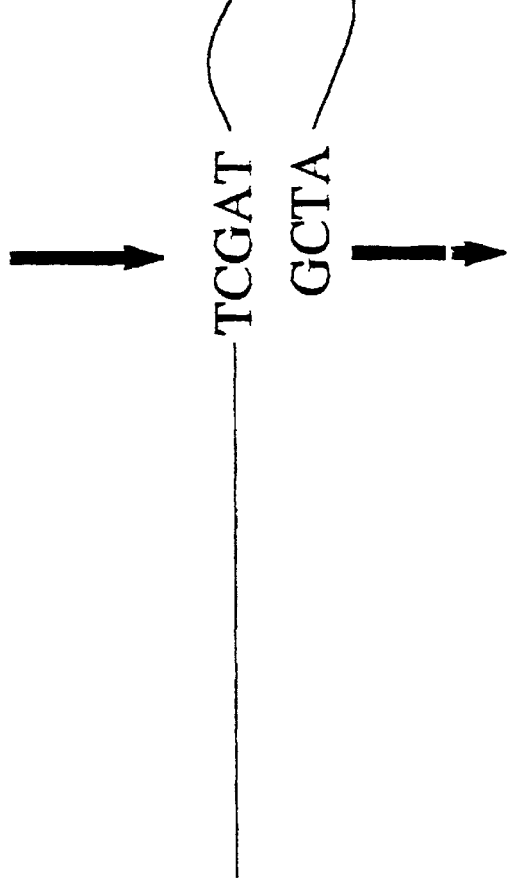

SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: Hypothetical sequence

<400> SEQUENCE: 1
taaaacgtcg ccgccttcga ttgatggcga tcg        33

<210> SEQ ID NO 2
<211> LENGTH: 34
<212> TYPE: DNA
<213> ORGANISM: Artificial Sequence
<220> FEATURE:
<223> OTHER INFORMATION: Hypothetical sequence -continued

<400> SEQUENCE: 2
taaaacgtcg ccgccttcga ttgatggcga tcga                    34

METHODS FOR SELECTING PRIMERS

RELATED APPLICATIONS

This application claims the benefit of U.S. Application Ser. No. 60/154,550, filed Sep. 17, 1999, the entire teachings of which are incorporated herein by reference.

BACKGROUND OF THE INVENTION

Nucleic acid analysis techniques that identify alterations or polymorphisms within known sequences are useful in many aspects of scientific, medical and forensic fields. For example, these techniques can be used in the genotyping of individuals in order to diagnose hereditary diseases or provide prognosis based on known genetic lesions. These techniques can also be used for clinical purposes such as tissue typing for histocompatibility or for forensic purposes such as identity or paternity determination. Furthermore, nucleic acid analysis techniques can be used for the identification of organisms or to distinguish or identify pathogenic organisms or infectious agents. In addition, these techniques are useful in the identification and monitoring of genetically modified agricultural organisms such as crops and livestock. As genomic sequence of organisms from bacteria to humans become known, the need for nucleic acid analysis techniques that are rapid and inexpensive increases.

Probe- or primer-based assays are useful in the detection, quantitation and analysis of nucleic acids. Nucleic acid probes are used to analyze samples for the presence of nucleic acid sequences from bacteria, fungi, viruses or other organisms and are also useful in examining genotypes, genetically-based disease states or clinical conditions of interest. Genotypes of interest include, for example, point mutations, deletions, insertions and inversions. Furthermore, these assays are useful to detect and monitor polymorphisms within nucleic acid sequences of interest.

Unfortunately, there are a number of potential and actual sources of error in hybridization based assays. For example, pseudogenes (gene duplication) may cause errors in identifying the appropriate target during PCR. Moreover, mispriming of primers and undesired hybridization between primers and other primers and between primers and unintended targets is also a concern.

SUMMARY OF THE INVENTION

As described herein, it has been discovered that the phenomenon of "foldback" within a primer is a source of error in hybridization-based assays, and particularly in single-base extension (SBE) assays. SBE assays for, e.g., identifying and analyzing polymorphisms, are based on single-base extension of a primer with a fluorescently-labeled dideoxynucleotide. Single-base extension occurs in a template-dependent manner, and each distinct nucleotide can be labeled with a distinct detectable fluorescent label. Once the labeled dideoxynucleotide is incorporated onto the primer, the fluorescence of the primer is assessed by any of several methods to determine which dideoxynucleotide was incorporated, and, accordingly, which nucleotide was present at the position of interest. Thus, it will be appreciated that the primer must hybridize to the appropriate locus on the target sequence in order to generate an accurate signal by SBE. The phenomenon of primer foldback interferes with this accuracy.

As shown in FIG. 1, foldback occurs when a portion of the primer is the reverse complement of another portion of the primer. The intra-molecular interaction within the primer is stronger than the inter-molecular interaction between the primer and the target, and the primer folds back on itself to create a hairpin structure in the primer. The primer can then undergo single base extension based on the sequence of the primer adjacent to the intra-molecular hybridization rather then on the sequence of the intended target.

Thus, the present invention relates to a method for selecting primers which have a reduced incidence of undesired interactions. The method comprises subjecting one or more primers to analysis to identify primers in which the 3' end or the 5' end of the primer hybridizes to another portion of the primer sequence and excluding identified primers, wherein the remaining primers have a reduced incidence of undesired interactions. In a particular embodiment, the method comprises identifying primers in which: (1) at least 4 bases (nucleotides) (the reverse complementary region) from either the 3' or the 5' end of the primer exhibit reverse complementarity to 4 bases elsewhere on the primer (the homologous sequence); and (2) a 2-base span exists between the reverse complementary region and the homologous sequence.

In one embodiment, the primers are selected for use in SBE-based assays. In the method according to this embodiment, the method comprises subjecting one or more primers to analysis to identify primers in which the 3' end (where single-base extension occurs) hybridizes to another portion of the primer sequence. More specifically, the method comprises identifying primers in which: (1) at least 4 bases (the reverse complementary region) from the 3' end exhibit reverse complementarity to 4 bases elsewhere on the primer (the homologous sequence); (2) at least 1 base 5' to the reverse complementary region of the primer is exposed to allow SBE to occur; and (3) there exists a 2-base span between the reverse complementary region and the homologous region.

In a particularly preferred embodiment, the analysis is carried out using a processing means (e.g., a computer) to assess the nucleotide sequence of one or more primers. A variety of data processor programs and formats can be used to store the nucleotide sequence information of the primers on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention. This computer readable form can then be subjected to processing steps suitable for carrying out the analysis of the method.

For example, with respect to primers for use in SBE, the processing means can be programmed to determine all possible matches within a given nucleotide sequence, wherein the shortest possible match sequence extends from the 3' end and includes 4 bases and the longest possible match sequence extends from the 3' end to the halfway point of the nucleotide sequence. For each possible match, from longest to shortest, the processing means queries whether there is a homologous sequence in the rest of the primer, from the second 5' base to 2 bases from the possible match sequence. If so, the processing means reports the primer and match information and proceeds to test the nucleotide sequence of the next primer. Primers reported by the processing means are excluded from use in the SBE assay.

Primers selected by the methods of the present invention retain all of the advantages and uses of traditionally-selected primers but have the advantage of a reduced incidence of unwanted interactions (e.g., foldback).

The invention also pertains to methods of improving the accuracy of SBE-fluorescence polarization (SBE-FP) methods. These methods include decreasing the dideoxynucleotide and primer concentrations used, and/or utilizing SBE primers of a length sufficient to reduce formation of secondary structures in the primers (e.g., hairpin structures resulting from foldback).

BRIEF DESCRIPTION OF THE DRAWING

FIG. 1 is an illustration of the foldback phenomenon. As illustrated with a hypothetical SBE primer, foldback occurs when a portion of the primer is the reverse complement of another portion of the primer. The intra-molecular interaction within the primer is stronger than the inter-molecular interaction between the primer and the target, and the primer folds back on itself to create a hairpin structure in the primer. The primer can then undergo single base extension based on the sequence of the primer adjacent to the intra-molecular hybridization rather then on the sequence of the intended target.

DETAILED DESCRIPTION OF THE INVENTION

Probe- or primer-based assays are useful in the detection, quantitation and analysis of nucleic acids. Nucleic acid probes are used to analyze samples for the presence of nucleic acid sequences from bacteria, fungi, viruses or other organisms and are also useful in examining genotypes, genetically-based disease states or clinical conditions of interest. These assays typically rely on nucleic acid hybridization. Sequence differences of a single base (e.g., point mutation) in very short oligomers (e.g., <10 base pairs ("bp")) can be sufficient to enable the discrimination of the hybridization to complementary nucleic acid target sequences as compared with non-target sequences. However, nucleic acid probes of greater than 10 bp in length are often preferred or required to obtain the sequence specificity necessary to correctly identify a unique organism, disease state or clinical condition of interest.

As described herein, it has been discovered that the phenomenon of "foldback" within a primer is a source of error in hybridization-based assays, and particularly in single-base extension (SBE) assays. SBE assays for, e.g., identifying and analyzing polymorphisms, are based on single-base extension of a primer with a fluorescently-labeled dideoxynucleotide. Single-base extension occurs in a template-dependent manner, and each distinct nucleotide can be labeled with a distinct detectable fluorescent label. Once the labeled dideoxynucleotide is incorporated onto the primer, the fluorescence of the primer is assessed by any of several methods to determine which dideoxynucleotide was incorporated, and, accordingly, which nucleotide was present at the position of interest. Thus, it will be appreciated that the primer must hybridize to the appropriate locus on the target sequence in order to generate an accurate signal by SBE. The phenomenon of primer foldback interferes with this accuracy.

As shown in FIG. 1, foldback occurs when a portion of the primer is the reverse complement of another portion of the primer. The intra-molecular interaction within the primer is stronger than the inter-molecular interaction between the primer and the target, and the primer folds back on itself to create a hairpin structure in the primer. The primer can then undergo single base extension based on the sequence of the primer adjacent to the intra-molecular hybridization rather then on the sequence of the intended target.

Thus, the present invention relates to a method for selecting primers which have a reduced incidence of undesired interactions. The method comprises subjecting one or more primers to analysis to identify primers in which the 3' end or the 5' end of the primer hybridizes to another portion of the primer sequence and excluding identified primers, wherein the remaining primers have a reduced incidence of undesired interactions. In a particular embodiment, the method comprises identifying primers in which: (1) at least 4 bases (nucleotides) (the reverse complementary region) from either the 3' or the 5' end of the primer exhibit reverse complementarity to 4 bases elsewhere on the primer (the homologous sequence); and (2) a 2-base span exists between the reverse complementary region and the homologous sequence.

In one embodiment, the primers are selected for use in SBE-based assays. In the method according to this embodiment, the method comprises subjecting one or more primers to analysis to identify primers in which the 3' end (where single-base extension occurs) hybridizes to another portion of the primer sequence. More specifically, the method comprises identifying primers in which: (1) at least 4 bases (the reverse complementary region) from the 3' end exhibit reverse complementarity to 4 bases elsewhere on the primer (the homologous sequence); (2) at least 1 base 5' to the reverse complementary region of the primer is exposed to allow SBE to occur; and (3) there exists a 2-base span between the reverse complementary region and the homologous region.

In a particularly preferred embodiment, the analysis is carried out using a processing means (e.g., a computer) to assess the nucleotide sequence of one or more primers. A variety of data processor programs and formats can be used to store the nucleotide sequence information of the primers on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention. This computer readable form can then be subjected to processing steps suitable for carrying out the analysis of the method.

For example, with respect to primers for use in SBE, the processing means can be programmed to determine all possible matches within a given nucleotide sequence, wherein the shortest possible match sequence extends from the 3' end and includes 4 bases and the longest possible match sequence extends from the 3' end to the halfway point of the nucleotide sequence. For each possible match, from longest to shortest, the processing means queries whether there is a homologous sequence in the rest of the primer, from the second 5' base to 2 bases from the possible match sequence. If so, the processing means reports the primer and match information and proceeds to test the nucleotide sequence of the next primer. Primers reported by the processing means are excluded from use in the SBE assay.

The selection method of the present invention is applicable to any method which utilizes primer hybridization to a target sequence. However, the selection method is particularly applicable to SBE-based methods. For example, methods such as Chen et al., (*PNAS* 94:10756–61 (1997), incorporated herein by reference) use a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide. Such methods are useful, for example, for identifying and analyzing polymorphisms. Other SBE-based methods are shown, for example, in Chen et al., *Genome Research* 9(5):492–498 (1999) (incorporated herein by reference).

The primer selection method is also useful in other methods, such as that described in U.S. application Ser. No. 09/536,841, filed Mar. 27, 2000, by Fan et al.

As used herein, the term primer is defined as any oligomer suitable for hybridizing to a target. Primers include oligomers of ribonucleic acid and deoxyribonucleic acid. Primers are typically from about 6 to about 60 nucleotides in length, more preferably from about 40 to about 52 nucleotides in length, and most preferably, from about 16 to about 25 nucleotides in length.

Primers typically comprise a target-specific portion designed to hybridize to a target nucleic acid sequence, if present, under suitable hybridization conditions. For SBE, for example, the length and composition of the primer will generally be chosen such that a complex is formed between the primer and the target sequence suitable to allow the primer to direct template-dependent synthesis. Primers suitable for hybridization to a particular target can readily be determined by the skilled artisan using methods known in the art.

For example, the skilled artisan will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a primer/target combination is often found by the well known technique of fixing several of the aforementioned stringency factors and then determining the effect of varying a single stringency factor. Optimal stringency for an assay may be experimentally determined by examining variations of each stringency factor until the desired degree of discrimination between the variable region and target sequences has been achieved. The level of assay stringency will increase or decrease depending on whether the target and variable regions are complementary or substantially complementary.

The invention also pertains to methods of improving the accuracy of SBE-fluorescence polarization (SBE-FP) methods. As used herein, SBE-FP is a method by which SBE products are detected by subjecting the sample to polarized light and distinguishing between large fluorescent molecules which polarize light (e.g., the fluorescent-labeled nucleotide incorporated into the primer), and small fluorescent molecules which do not polarize light (e.g., unincorporated fluorescent-labeled nucleotides). For a discussion of fluorescence polarization, see, for example, Jolley et al., *Clin Chem.* 27(9):1575–1579 (1981); Popelka et al., *Clin Chem.* 27(7):1198–1201 (1981); Dandliker et al., *Immunochemistry* 10:219–227 (1973); Dandliker and de Saussure, *Immunochemistry* 7:799–828 (1970); Wang et al., U.S. Pat. No. 5,391,740; Jolley, *J. Anal Tox.* 5(5):236–240 (1981)). This method is capable of distinguishing between the free fluorescent-labeled nucleotides and the fluorescent-labeled nucleotides incorporated into the primer. The fluorescence polarization method is based on the relationship between size and Brownian motion or spinning in solution. The free fluorescent nucleotide is smaller than the fluorescent nucleotide incorporated into the primer. As molecular size increases, the rate of spinning decreases, resulting in a greater degree of fluorescent polarization (Weber, *Adv. Protein Chem.* 8:415–459 (1953)); fluorescence polarization can be measured in a fluorescence polarimeter. Methods of this embodiment include decreasing the dideoxynucleotide and primer concentrations used, and/or utilizing SBE primers of a length sufficient to reduce formation of secondary structures in the primers (e.g., hairpin structures resulting from foldback).

The teachings of all references cited herein are incorporated herein by reference in their entirety.

What is claimed is:

1. A method for selecting primers which have a reduced incidence of undesired interactions comprising identifying primers in which:
   a) at least 4 nucleotides of the primer exhibit reverse complementarity to 4 nucleotides elsewhere on the primer;
   b) there exists a span of sufficient size between the nucleotides that exhibit reverse complementarity to allow the primer to fold back on itself; and
   c) there is at least one nucleotide 5' of the reverse complementary nucleotides which are the most 5' in said primer, wherein identified primers are excluded and the remaining primers have a reduced incidence of undesired interactions.

2. A method for selecting primers which have a reduced incidence of undesired interactions comprising identifying primers in which:
   a) at least 4 nucleotides of the primer exhibit reverse complementarity to 4 nucleotides elsewhere on the primer;
   b) there exist at least 2 nucleotides between the nucleotides that exhibit reverse complementarity; and
   c) there is at least one nucleotide 5' of the reverse complementary nucleotides which are the most 5' in said primer, wherein identified primers are excluded and the remaining primers have a reduced incidence of undesired interactions.

* * * * *

UNITED STATES PATENT AND TRADEMARK OFFICE
CERTIFICATE OF CORRECTION

PATENT NO. : 6,440,675 B1
DATED : August 27, 2002
INVENTOR(S) : Kerstin A. Lindblad-Toh, Ellen Winchester, Joel N. Hirschhorn and Pamela Sklar It is certified that error appears in the above-identified patent and that said Letters Patent is hereby corrected as shown below:

<u>Title page,</u>
Item [73], Assignee, after "Whitehead Institute for Biomedical Research, Cambridge, MA (US), please insert -- and The General Hospital Corporation, Boston, MA (US) --.

Signed and Sealed this

Fourteenth Day of January, 2003

JAMES E. ROGAN
*Director of the United States Patent and Trademark Office*